United States Patent
De Cesaris et al.

(10) Patent No.: US 6,254,640 B1
(45) Date of Patent: Jul. 3, 2001

(54) SHAFT PROSTHESIS AND SET

(75) Inventors: Alessandro De Cesaris, Winterthur; Manfred Menzi, Baar, both of (CH); Wolfhart Puhl, Ulm (DE)

(73) Assignee: Sulzer Orthopaedie AG, Baar (CH)

( * ) Notice: Subject to any disclaimer, the term of this patent is extended or adjusted under 35 U.S.C. 154(b) by 0 days.

(21) Appl. No.: 09/322,241

(22) Filed: May 28, 1999

(30) Foreign Application Priority Data

Jun. 4, 1998 (EP) .................................................. 98810510

(51) Int. Cl.⁷ ........................................................ A61F 2/36
(52) U.S. Cl. ....................................... 623/23.35; 623/23.15
(58) Field of Search ............................ 623/23.15, 23.28, 623/23.35, 23.44, 22.11, 16.11, 18.11, 22.4, 22.41, 23.26, 23.31

(56) References Cited

U.S. PATENT DOCUMENTS

| | | | |
|---|---|---|---|
| Re. 32,488 | * 9/1987 | Gustilo et al. | 623/23.35 |
| 3,740,769 | * 6/1973 | Haboush | 623/23.35 X |
| 4,658,808 | * 4/1987 | Link . | |
| 4,738,681 | * 4/1988 | Koeneman et al. | 623/23.35 |
| 4,871,369 | * 10/1989 | Muller | 623/23.35 |
| 4,995,883 | * 2/1991 | Demane et al. . | |
| 5,358,534 | * 10/1994 | Dudasik et al. | 623/23.35 |
| 5,458,651 | * 10/1995 | Lawes | 623/23.15 |
| 5,755,811 | * 5/1998 | Tanamal et al. | 623/23.35 |
| 5,776,204 | * 7/1998 | Noble et al. . | |
| 6,030,417 | * 2/2000 | Bresler et al. . | |

FOREIGN PATENT DOCUMENTS

| | | |
|---|---|---|
| 25 37 807 | 3/1976 | (DE) . |
| 0477113A1 | 3/1992 | (EP) . |
| 0672396A2 | 9/1995 | (EP) . |
| 0738503A1 | 10/1996 | (EP) . |
| 2610822 | 8/1988 | (FR) . |
| 2629707 | 10/1989 | (FR) . |
| 2641462 | 7/1990 | (FR) . |
| 2720931 | 12/1995 | (FR) . |
| 2729292 | 7/1996 | (FR) . |
| 2735970 | 1/1997 | (FR) . |

* cited by examiner

*Primary Examiner*—Jeffrey A. Smith
(74) *Attorney, Agent, or Firm*—Townsend and Townsend and Crew LLP

(57) ABSTRACT

The shaft prosthesis (1) has a distal section (2) with a substantially circular cross-section and a proximal section (3) adjoining this distal section (2). A rib (4) is located at the lateral side of the prosthesis and protrudes in the ventral direction. The proximal section (3) enlarges in the upward direction. A neck (5) is provided in the upper end region on which a joint ball can be attached. The diameter of the shaft prosthesis (1) enlarges substantially conically on all sides starting from the distal end of the shaft prosthesis (1).

7 Claims, 4 Drawing Sheets

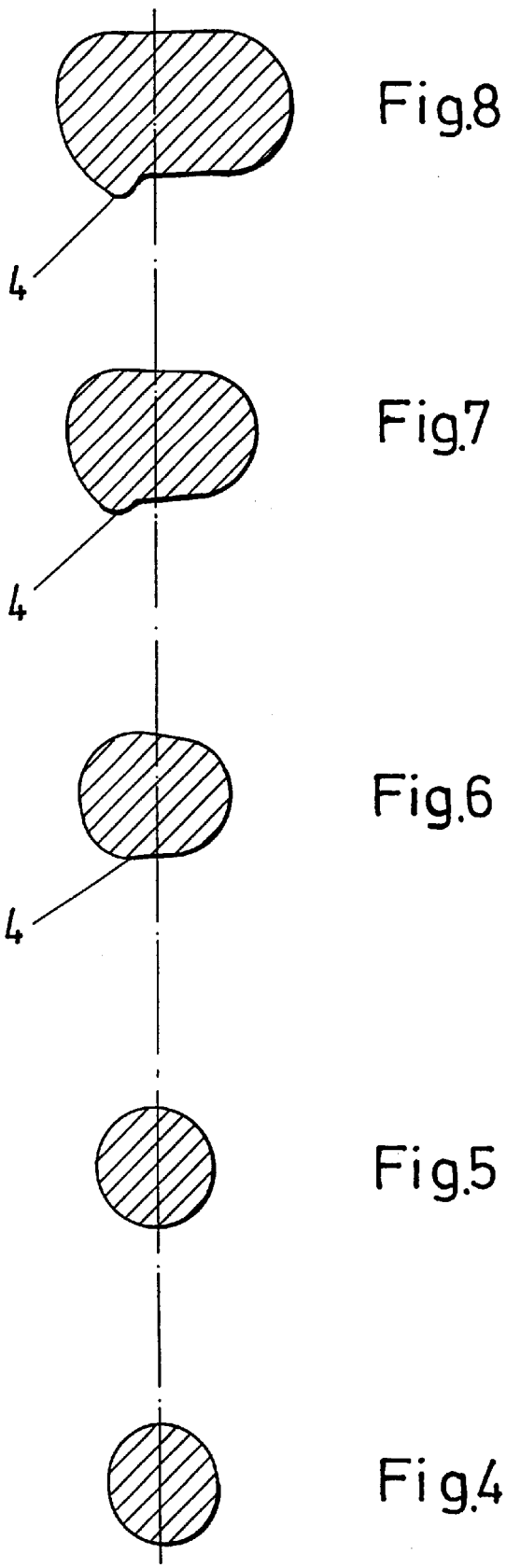

SHAFT PROSTHESIS AND SET

BACKGROUND OF THE INVENTION

The invention relates to a shaft prosthesis in accordance with the preamble of the independent patent claim.

Shaft prostheses, especially those for the implantation in the femur, are available on the market in numerous different embodiments. With regard to the manner of the anchoring of the prosthesis in the femur, one can distinguish, the shaft prostheses into cemented and cement-free prostheses. In this it is determined in the planning of the operation whether a cemented or cement-free anchoring of the prostheses comes under consideration as a result of the information about the bone, e.g. on the size of the femur and on its condition, which the orthopedist receives from X-ray photographs, etc. In addition the size of the respective prosthesis which is to be implanted is also determined.

During the operation it is then assumed that a given kind of anchoring is carried out, e.g. a cemented anchoring. Prostheses which are suitable for an anchoring of this kind are known for example from DE-B2-25-37 807 or from EP-A-0,672,396. During the operation the femur is first prepared by the orthopedist. Simply expressed, in this situation a cavity is produced into which the cement is then introduced. Subsequently the prosthesis is introduced into the cement and held in place until the cement hardens and the prosthesis is thus fixed. The introduction of the prosthesis into the cement must take place in such a manner that no inclusions of air arise in the cement. This introduction requires a certain skill on the part of the orthopedist since the cement is so constituted by its flow properties at the time point of the introduction into the femur that a flowing back of cement which has once been displaced practically does not take place. This is correspondingly reflected in the design of the shaft—the design of prostheses to be cemented differs considerably from the design of prostheses to be anchored without cement because the anchoring of cemented prostheses takes place in the cement jacket which surrounds the prosthesis, whereas in prostheses to be anchored without cement the anchoring takes place directly in the bone tissue surrounding the prosthesis.

The decision as to whether a prosthesis is anchored with cement or without cement in the implantation is thus made prior to the operation, namely in the pre-operative planning. The decision on the size of the prosthesis to be implanted is also already made prior to the operation. These decisions then also decide how the cavity to be produced by the orthopedist for the reception of the cement must look or which dimensions it must have respectively.

In several cases it turns out during the operation, namely during the preparation of the femur, however, that, for example as a result of the condition of the bone material, it is possible or even desirable to provide a cement-free anchoring although a cemented anchoring had been planned. At this time point however a change in the decision for the cemented prosthesis is no longer possible because for this a new operation planning must take place as a result of the different shaft design of the prostheses to be anchored with cement and without cement.

SUMMARY OF THE INVENTION

An object of the invention is thus to propose a shaft prosthesis which enables a decision with respect to the anchoring which had already taken place in the operation planning to be changed once again without a new planning being required for this. This means in other words that the prosthesis must be suitable by virtue of its design both for a cemented and for a cement-free anchoring.

In accordance with the invention this object is satisfied by a shaft prosthesis which has a distal section which has a substantially circular cross-section. This means that this distal section is preferably designed to be completely circular, but that slight deviations from the circular shape such as e.g. flattenings in order to ensure a sufficiently thick cement jacket in cemented anchorings are however possible. At this distal section there adjoins a proximal section at which a rib which protrudes in the ventral direction is provided at the lateral side. The proximal section of the shaft prosthesis enlarges in the upward direction and a neck is provided in the upper end region on which a joint ball can be attached. The diameter of the shaft prosthesis enlarges substantially conically on all sides (see above), preferably conically on all sides, starting from the distal end of the shaft prosthesis. A shaft prosthesis of this kind is basically suitable for a cemented as well as for a cement-free anchoring in the bone.

The substantially all-sided conical extension starting from the distal end of the shaft prosthesis means that the prosthesis has no undercuttings which can otherwise lead to air enclosures in a cemented anchoring due to the poor flow properties (high viscosity) of the bone cement. In addition the enlargement of the shaft in the proximal direction leads to a compression of the bone cement and thereby to better distribution of the cement into cavities in the often porous bones (spongiosa). Moreover, a conical enlargement which already starts from the distal end of the prosthesis corresponds to the natural shape of the marrow chamber in the diaphysary bone region. In shaft prostheses with non-conical cylindrical distal end regions, namely, stoppages of prostheses of this kind can partially arise in the cement-free anchoring, the anchoring of which prostheses should however preferably take place in the proximal region of the prosthesis. A stoppage of this kind then means an additional work step for the orthopedist since he must then in addition bore open the marrow chamber, which had been prepared with a conical rubbing awl, in order that the prosthesis can be introduced still further into the marrow chamber in order that it can be anchored in the proximal end region.

In an advantageous exemplary embodiment of the shaft prosthesis in accordance with the invention the opening angle in the region of the conically enlarging distal section lies in the range from 1° to 10°; in particular it amounts to about 2°. Practically all shapes of the marrow chamber in the diaphysary bone region which occur are covered by this range; a not infrequently occurring shape has an opening angle of 2°.

In a further advantageous exemplary embodiment of the shaft prosthesis in accordance with the invention the angle between the longitudinal axis of the shaft and the neck axis lies in the range from 120° to 150°; in particular it amounts to approximately 135°. In the case of this angle one also speaks of the so-called "CCD angle" (Centrum Collum Diaphysis angle). The important cases occurring in practice are likewise covered by the named region. A CCD angle of 135° is frequently encountered in younger patients; however a prosthesis with a CCD angle of this size is also implantable for patients of advanced age. With such a CCD angle e.g. a tautening of the partially slackened ligament apparatus can be effected because the natural CCD angle at the bone of the patient was lower prior to the implantation of the prosthesis and the ligament apparatus is again "tautened" through the greater CCD angle.

In a further exemplary embodiment of the shaft prosthesis in accordance with the invention the shaft prosthesis is inclined in the anterior direction in the proximal section, with this angle of inclination or anteversion (anteversion angle is the frequently encountered designation) lies in the range from 5° to 17°, and amounts in particular to approximately 11°. This angle range includes the most frequently occurring anteversion angle; a very frequently occurring value for this angle amounts to approximately 11°.

A further aspect of the present invention relates to a series of shaft prostheses of different sizes, with the individual shaft prostheses of a series of this kind being formed as described above. The shaft prostheses of different sizes are built up according to the onion skin principle, with the thickness dimensions of two successive sizes differing by a constant amount. The length of two successive sizes can likewise differ by a constant amount, which can however deviate from the amount of the thickness difference.

Different philosophies exist in the case of the cemented anchoring with respect to the thickness of the cement jacket which surrounds the implanted prosthesis, namely philosophies which start from a very thin cement jacket (e.g. a few tenths of a millimeter) and those which start from a thicker cement jacket (e.g. in the range from one up to three millimeters). In this the cement jacket is understood to mean the intermediate space between the prepared implant cavity and the prosthesis which is filled with cement. It is clear that an intrusion of cement into the spongiosa can lead to a thickening of this cement jacket in practice. In particular in regard to the latter philosophy (thick cement jacket) a further aspect of the present invention relates to a set of shaft prostheses which comprises two series of shaft prostheses—a first and a second series—with the prostheses of a series being designed as described above. The first series contains shaft prostheses for cement-free implantations and the second series of shaft prostheses contains those for cemented implantations. In this the shaft prostheses of the different series are identical in regard to their design and to their size to the corresponding shaft prostheses in the other series, however that shaft prosthesis in the second series (prostheses for cemented anchoring) which corresponds to a shaft prosthesis for cement-free implantation in the first series is smaller than the corresponding shaft prosthesis in the first series. Only the neck of the shaft prosthesis in the second series (prostheses for cemented anchoring) corresponds approximately to the size of the neck of the corresponding prosthesis in the first series (cement-free anchoring), through which in regard to the neck of the prosthesis the size is approximately equally large as in the cement-free anchoring; the prosthesis to be anchored is itself however smaller than the corresponding prosthesis for a cement-free anchoring.

Further advantageous embodiments of the invention result from the exemplary embodiments which are described below.

BRIEF DESCRIPTION OF THE DRAWINGS

FIGS. 4–8 are sections through the exemplary embodiment of the shaft prosthesis of FIG. 2 along the lines IV—IV, V—V, VI—VI, VII—VII and VIII—VIII.

DESCRIPTION OF THE PREFERRED EMBODIMENTS

Figure 1:
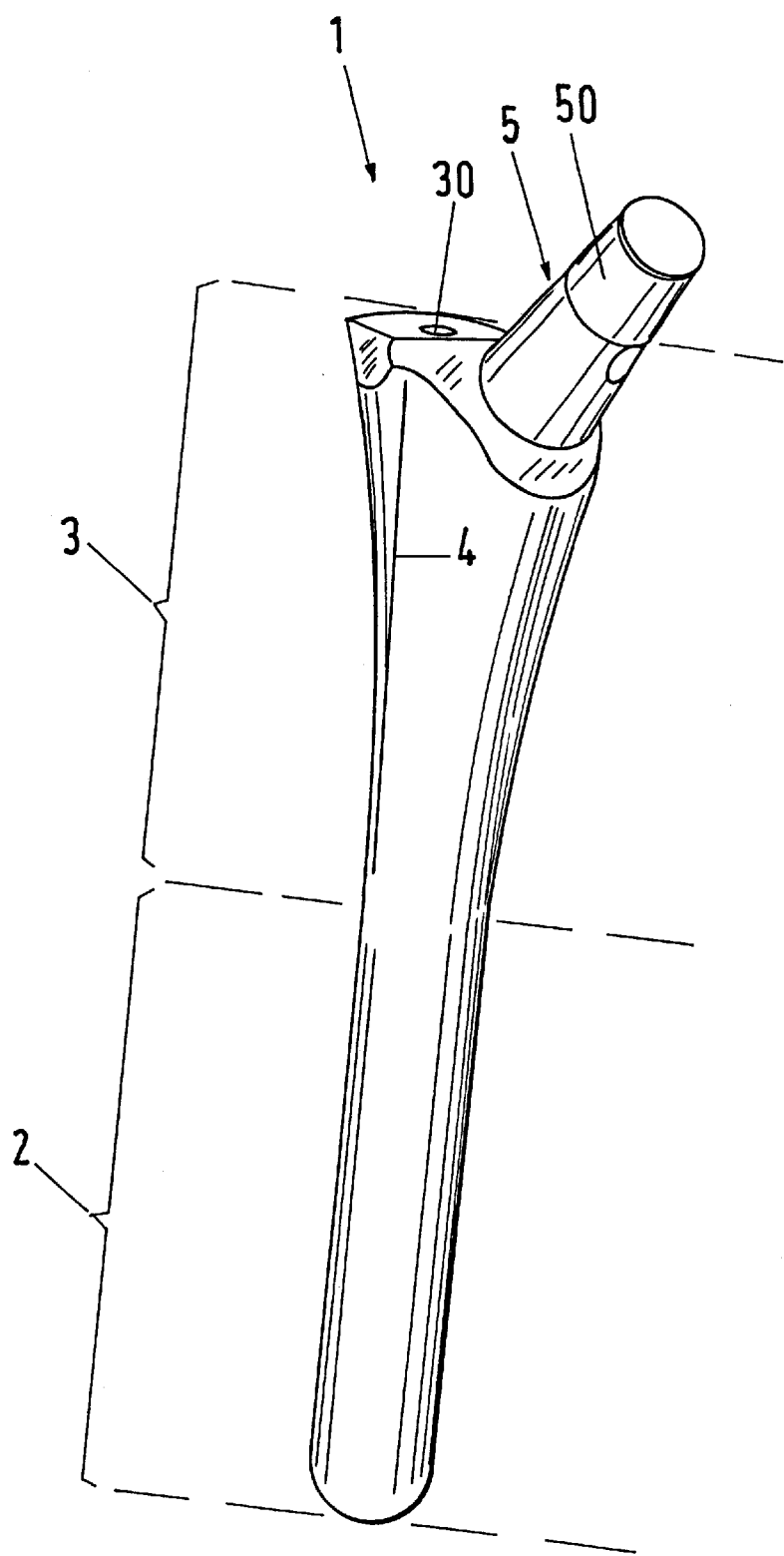
FIG. 1 is an exemplary embodiment of a shaft prosthesis in accordance with the invention in a perspective illustration.

FIG. 1 shows an exemplary embodiment of a shaft prosthesis in accordance with the invention in a perspective view from the medial/ventral direction. The shaft prosthesis 1 comprises a distal section 2 and a proximal section 3 adjoining this distal section. At the upper end of the proximal section 3 a depression 30 for the application of a striking-in instrument for cement-free anchoring or for the application of a pressing-in instrument for cemented anchoring can be recognized. A rib 4 protrudes in the ventral direction at the lateral side at the proximal section 3. This rib 4 follows approximately the anatomical form of the bone in the lateral region. In the upper end region of the proximal section 3 of the shaft prosthesis 1 there adjoins a neck 5 to which a joint ball (not illustrated) can be attached. This takes place in the illustrated exemplary embodiment in such a manner that a joint ball of a suitable material (e.g. of ceramic or of metal) formed with a conical blind bore is pushed onto the conically tapering neck piece 50 and is held via the cone clamping seat on the neck piece 50.

Figure 2:
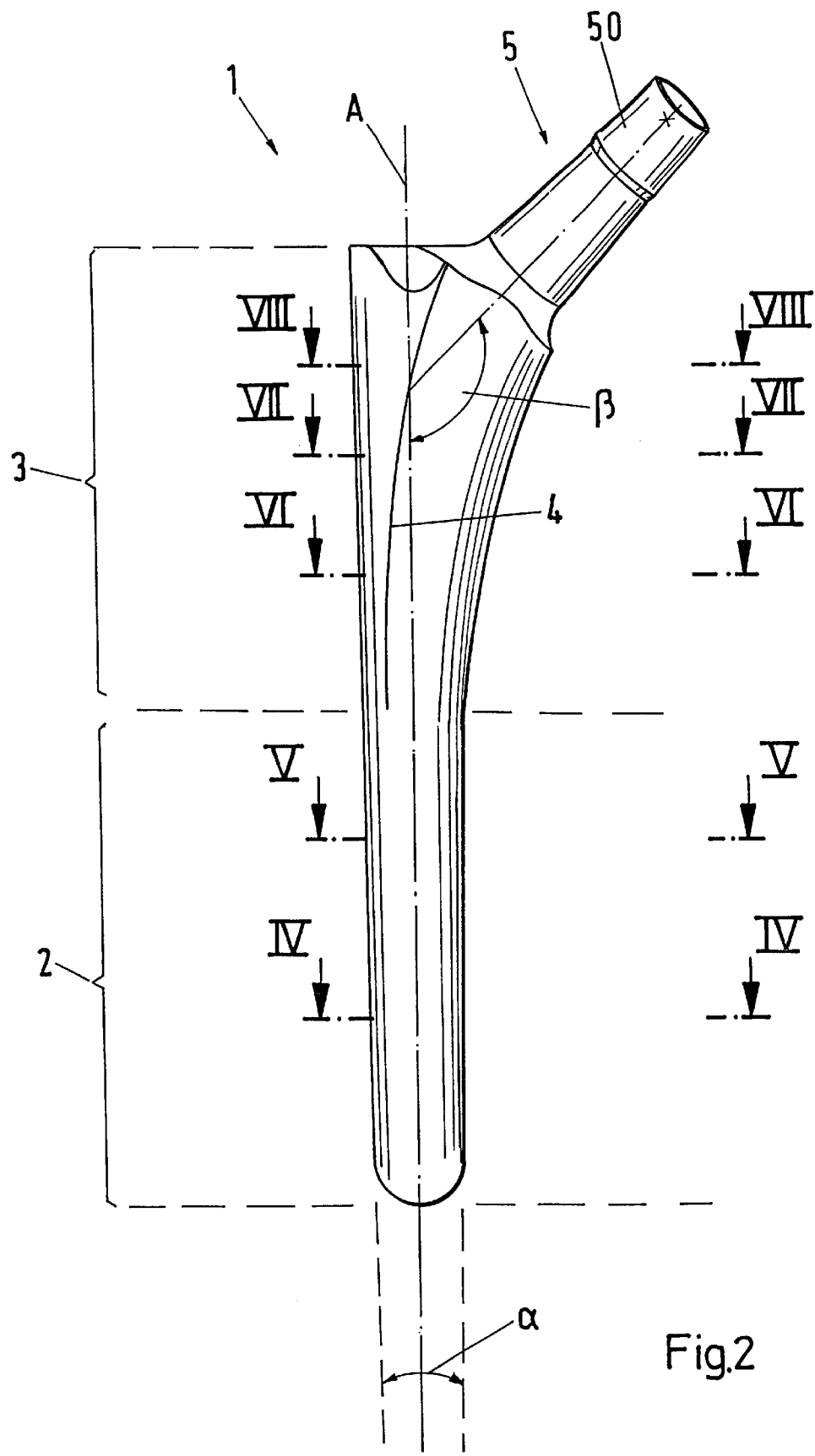
FIG. 2 is the exemplary embodiment of the shaft prosthesis in FIG. 1 in a ventral view.

In FIG. 2 the exemplary embodiment of the shaft prosthesis 1 of FIG. 1 can be recognized in a ventral view. One also recognizes here the adjoining distal section 2 and proximal section 3 of the shaft prosthesis 1. Furthermore, one recognizes the rib 4 which protrudes ventrally (that is, out of the plane of the drawing) and the neck 5 which adjoins in the upper end region of the proximal section. Furthermore, one recognizes in FIG. 2 that the diameter of the shaft prosthesis enlarges on all sides starting from the distal end of the shaft prosthesis. This is indicated in FIG. 2 with the help of the opening angle $\alpha$, which lies in the range from 1° to 10°. In particular it amounts to approximately 2°. One should imagine the opening angle $\alpha$ in FIG. 2 in such a manner that both the two broken lines which are illustrated at the end of the prosthesis (quasi as fictional extension of the outer contour of the prosthesis) and the axis A which is illustrated in chain-dotted lines are continued until the three lines intersect (which would only be the case far below the paper). The opening angle $\alpha$ is then included between the two broken lines.

Furthermore, one also recognizes in FIG. 2 the angle $\beta$, which the axis of the neck 5 includes with the shaft axis 10. This angle is also called the CCD angle (Centrum Collum Diaphysis angle). In the illustrated exemplary embodiment of the shaft prosthesis this CCD angle $\beta$ lies in the range from 120° to 150°, in particular it amounts to approximately 135°. A CCD angle of 135° in the femur is more frequently encountered in younger patients; in older patients it is smaller as a rule. Nevertheless a prosthesis with such a CCD angle is by all means implantable even in patients of advanced age. An implantation of a prosthesis with such a CCD angle can then result in a tautening of the partially slackened ligament apparatus in such patients; the ligament apparatus is thus quasi "tautened" again and activated through the greater CCD angle.

Moreover, in FIG. 2 one also recognizes the different sections IV—IV, V—V, VI—VI, VII—VII and VIII—VIII. The sections themselves are illustrated in FIGS. 4–8. In FIG. 4 one recognizes a cross-section in the distal section 2 of the shaft prosthesis 1. The cross-section is circular, which also holds for the cross-section V—V shown in FIG. 5 in the distal section 2. This cross-section is however greater in diameter than the cross-section IV—IV because of course the shaft prosthesis continuously enlarges on all sides starting from the distal end. The cross-section VI—VI shown in FIG. 6 is already located in the proximal section 3 of the prosthesis. There one already weakly recognizes the rib 4 which protrudes ventrally on the lateral side of the shaft prosthesis. In addition one recognizes that the shaft prosthesis still enlarges on all sides in the proximal section 3. One also recognizes this especially in FIG. 2.

In FIG. 7 the cross-section along the line VII—VII of FIG. 2 can be recognized in which the rib 4 protruding ventrally on the lateral side of the shaft prosthesis 1 can be recognized even more pronouncedly than in the cross-section along the line VI—VI. This ventrally protruding rib 4 can be most strongly pronouncedly recognized in FIG. 8, which shows a cross-section along the line VIII-VIII of FIG. 2.

In all, one recognizes from FIGS. 4–8 that the prosthesis 1 enlarges conically on all sides in the distal section 2 beginning directly from the distal end and that the enlargement of the prosthesis continues in the proximal section 3. This design of the prosthesis has on the one hand the advantage that no undercuttings exist, so that in cemented anchorings no air inclusions are to be feared, which could arise in the case of undercuttings because the bone cement is only poorly flowable (that is, highly viscous) when the prosthesis is introduced into the cement and a flowing back of cement which has already been displaced by the prosthesis does not take place. On the other hand this design of the prosthesis has the advantage that the all-sided conical enlargement of the prosthesis in the distal section 2 of the prosthesis which starts from the distal end facilitates the introduction of the prosthesis into the marrow chamber in the diaphysary region of the femur in particular also in cement-free anchorings because the marrow chamber is likewise formed to be slightly conically shaped in the diaphysary region of the femur. In non-conical cylindrical distal sections of prostheses on the contrary, stoppages can arise when introducing the prosthesis so that the orthopedist must then bore open the marrow chamber additionally in order to effect the proximal anchoring desired in cement-free anchorings. This would however mean an additional work step for the orthopedist in the preparation of the femur. In cemented anchorings a compression is effected onto the cement through the all-sided conical enlargement in the distal section 2 of the prosthesis and the subsequent enlargement in the proximal section 3 of the prosthesis and thereby to better distribution of the cement in cavities in the spongiosa.

Figure 3:
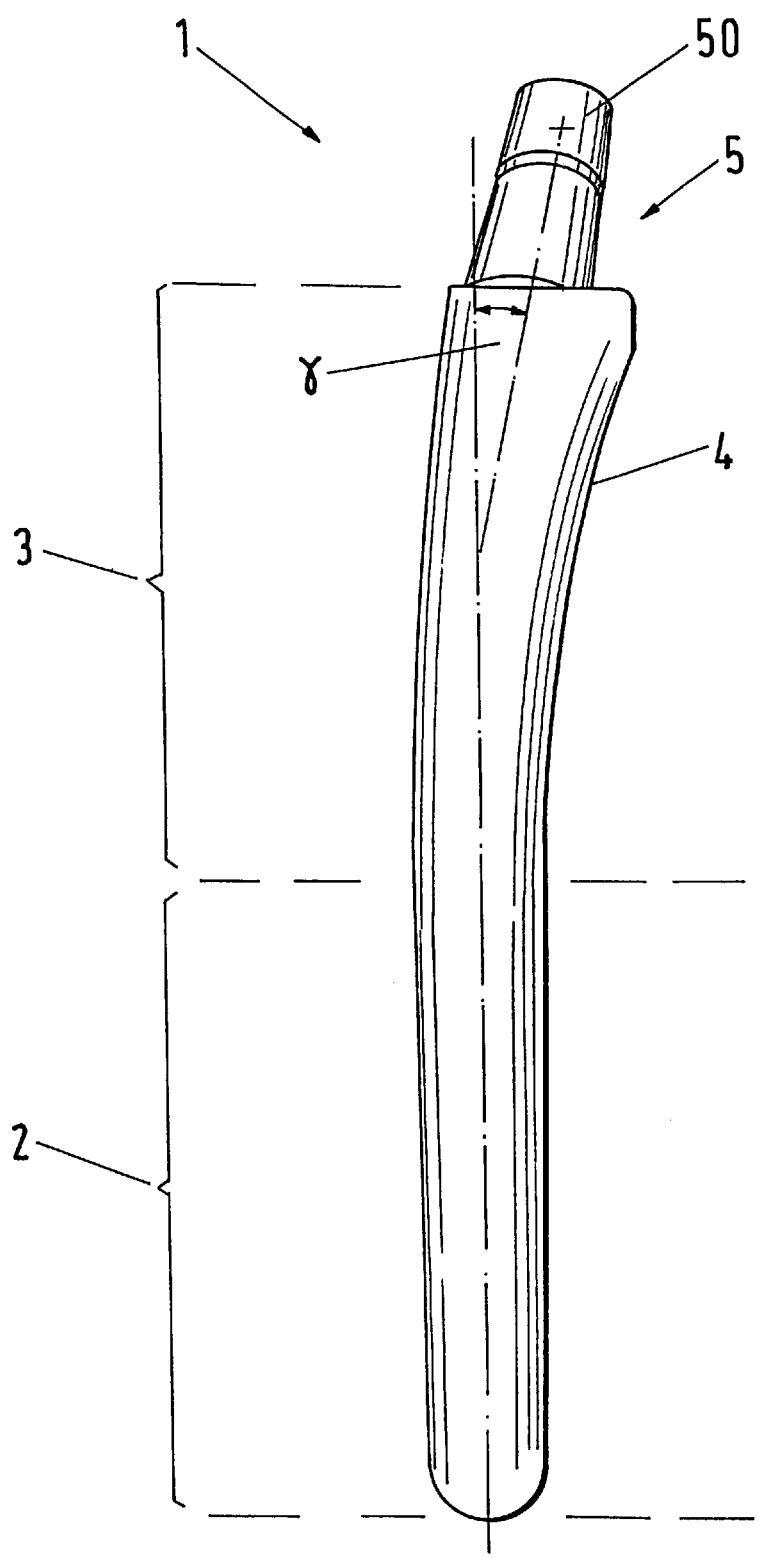
FIG. 3 is the exemplary embodiment of the shaft prosthesis in FIG. 1 in a view from lateral to medial.

Finally, FIG. 3 also shows the exemplary embodiment of the shaft prosthesis 1 of FIG. 1 in a view from lateral to medial. One likewise recognizes in this view the ventrally protruding rib 4. Furthermore, one also recognizes that the prosthesis is inclined in the direction towards the anterior in the proximal section. This angle of inclination γ, which is frequently also designated as the anteversion angle, lies in the range from 5° to 17°; in particular it amounts to approximately 11°. This range comprises the most frequently occurring values for the anteversion angle; the value of approximately 11° for the anteversion angle γ corresponds to one of the most frequently encountered values.

Since the femur sizes which occur can certainly differ strongly, an entire series of prostheses must be prepared in order to be able to cover the entire spectrum of femur sizes. In the pre-operative planning, a quite specific size of a prosthesis is admittedly determined for the patient; however it can ultimately turn out in the operation that either the next larger implant or the next smaller implant would possibly be better suited. For this reason a further aspect of the invention relates to a series of shaft prostheses of different sizes. The individual shaft prostheses of a series of this kind are formed as described above. The shaft prostheses of a series of this kind are built up in accordance with the so-called "onion skin principle", which means that the thickness dimensions of two successive sizes of shaft prostheses differ by a constant amount. The length dimensions of two successive sizes of shaft prostheses can also differ by a constant amount, which however can in turn be different from the difference in the thickness dimensions.

Different philosophies exist in particular in the anchoring of the prosthesis by means of bone cement. These differ essentially in the thickness of the cement jacket which surrounds the prosthesis (that is, the thickness of the cement layer between the cavity in the femur and the prosthesis). Some philosophies start from very thin cement jackets which lie in the range of several tenths of a millimeter; others start from cement jackets which lie in the range from approximately one to three millimeters. In particular in cement jackets which lie in the last named range it is to be sure very important in regard to the prosthesis size whether now a cemented or a cement-free anchoring takes place. If for example a cement-free anchoring had been planned pre-operatively and it turned out during the operation that a cemented anchoring is indicated, then a prosthesis which is significantly smaller with respect to the dimensions must be chosen. The neck of the smaller prosthesis for the cemented anchoring must however have substantially the same size as the neck of the prosthesis for the cement-free anchoring. Therefore a further aspect of the invention relates to a set of shaft prostheses, with this set of shaft prostheses comprising two series of prostheses which are formed as described above. Shaft prostheses for a cement-free anchoring are contained in a first series, whereas shaft prostheses for a cemented anchoring are contained in a second series. In this, for each individual prosthesis to be anchored without cement (from the first series) the set can either contain a corresponding prosthesis to be cemented (in the second series); it may however also be that e.g. for two adjacent sizes of prostheses to be anchored without cement only one prosthesis with an intermediate size for the cemented anchoring (in the second series) is contained in the set. That shaft prosthesis in the second series (cemented anchoring) which corresponds to a shaft prosthesis for a cement-free anchoring in the first series is smaller than the corresponding shaft prosthesis from the first series. The size of the neck of a prosthesis of this kind from the second series (cemented anchoring) corresponds however approximately to the size of the neck of the corresponding prosthesis for the cement-free anchoring, which also still enables an intra-operative decision in cement jackets of the mentioned size as to whether a cement-free or a cemented anchoring of the prosthesis is to take place.

It is self-evident that the materials for a shaft prosthesis which is to be anchored without cement and for a prosthesis to be cemented are different. Whereas titanium alloys are preferably used for prostheses which are to be anchored without cement due to the bio-compatibility of alloys of this kind (ultimately of course the bone must grow onto the prosthesis), for example cobalt-chromium-molybdenum alloys (CoCrMo alloys) come under consideration for prostheses to be cemented. Nevertheless the prostheses for cement-free anchoring and for cemented anchoring can by all means be of the same design since the design of the shaft prostheses is suitable for both kinds of anchoring.

What is claimed is:

1. Shaft prosthesis comprising a distal section having a substantially circular cross-section, a proximal section adjoining the distal section, and a rib which protrudes in a ventral direction and is located at a lateral side of the prosthesis, the proximal section enlarging in an upward direction, a neck provided at an upper end region of the proximal section for attaching a joint ball thereto, a diameter of the shaft prosthesis enlarging conically substantially on all sides starting from a distal end of the shaft prosthesis.

2. Shaft prosthesis in accordance with claim 1 wherein the distal section conically enlarges towards a proximal end of the prosthesis and defines an opening angle which is in the range from 1° to 10°.

3. Shaft prosthesis in accordance with claim 1 wherein an angle between a longitudinal axis of the prosthesis and an axis of the neck lies in the range from 120° to 150°.

4. Shaft prosthesis in accordance with claim 1 wherein the proximal section is inclined in an anterior direction at an angle of inclination in the range from 5° to 17°.

5. A set of shaft prostheses of differing sizes, each shaft prosthesis having a proximate end and a distal end and comprising a distal section having a substantially circular cross-section, a proximal section adjoining the distal section, a rib which protrudes in a ventral direction and is located at a lateral side of the prosthesis, the proximal section enlarging in a direction towards the proximate end, and a neck in a vicinity of the proximal end for attaching a joint ball thereto, a diameter of the shaft prosthesis enlarging substantially on all sides starting from the distal end of the shaft prosthesis towards the proximal end thereof, the set of shaft prostheses comprising shaft prostheses of differing sizes having thickness dimensions transverse to a longitudinal axis of the prosthesis which differ between successive sizes of the shaft prostheses of the set by a constant amount.

6. A set of shaft prostheses according to claim 5 comprising first and second series of shaft prostheses, the shaft prostheses of the first series being adapted for cement-free implantation and the shaft prostheses of the second series being adapted for cemented implantation, the shaft prostheses of the second series being smaller than corresponding shaft prostheses of the first series, the neck of the shaft prostheses of the first and second series having approximately like sizes.

7. A shaft prosthesis having proximal and distal ends and comprising a distal section and a proximal section joined to each other and which define a circumferentially substantially continuously convex shaft extending from the distal end to the proximal end and enlarging generally conically from the distal end towards the proximal end of the prosthesis, a rib located at a lateral side of the prosthesis and protruding in a ventral direction of the prosthesis, and a neck proximate the distal end which protrudes from the shaft for attaching a joint ball thereto.

* * * * *